US00PP12127P2

(12) United States Plant Patent
Zary

(10) Patent No.: US PP12,127 P2
(45) Date of Patent: Oct. 9, 2001

(54) HYBRID TEA ROSE PLANT NAMED 'JACSILHO'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/416,555

(22) Filed: Oct. 12, 1999

(51) Int. Cl.[7] ..... A01H 5/00
(52) U.S. Cl. ..... Plt./137
(58) Field of Search ..... Plt./137, 130, 141, Plt./148

(56) References Cited

U.S. PATENT DOCUMENTS

P.P. 1,143 * 11/1952 Boerner ..... Plt./148
P.P. 1,433 * 11/1955 Fisher ..... Plt./137

* cited by examiner

*Primary Examiner*—Howard J. Locker
(74) *Attorney, Agent, or Firm*—Klarquist Sparkman Campbell Leigh & Whinston, LLP

(57) ABSTRACT

A hybrid tea rose plant with free flowering, pinkish flowers having a high centered bud and open flower form on long stems; strong fragrance; and vigorous, upright, well-branched growth.

1 Drawing Sheet

The present invention relates to a new and distinct variety of rose plant of the hybrid tea class which was originated by me by crossing the variety Sterling Silver, (U.S. Plant Pat. No. 1,433), with the variety 'JAColite', (U.S. Plant Pat. No. 4,167).

The primary objective of this breeding was to produce a new rose variety having the bud and flower form and strong fragrance of the female parent, combined with the vigor, upright growth, long stems and flower production of the male parent. The objective was substantially achieved, along with other desirable improvements, as evidenced by the following unique combination of characteristics that are outstanding in the new variety and that distinguish it from its parents, as well as from all other varieties of which I am aware:

1. High centered bud and open flower form;
2. Strong fragrance;
3. Vigorous, upright, well-branched growth;
4. Free flowering; and
5. Long stems.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Sterling Silver' (U.S. Plant Pat. No. 1,433).

*Pollen parent.*—'JAColite' (U.S. Plant Pat. No. 4,167).

Classification:

*Botanical.*—*Rosa hybrida.*

*Commercial.*—Hybrid Tea.

FLOWER

Observations made from specimens grown in a garden environment at Somis, Calif. from March 1998 to August 1999.

Blooming habit: Continuous.

Bud:

*Size.*—1¾ inches long when the petals start to unfurl.

*Form.*—The bud form is long; pointed ovoid.

*Color.*—When sepals first divide, bud color is Yellow-White Group 158B with small areas and spots of Red Group 53C. When half blown, the upper sides of the petals are Red Group 49D, except the lower ¼ of the petal, which is Yellow Group 11C with a darker yellow color spot; and the lower sides of the petals are Red Group 49C, except on the petal edge where there is a borderof Red Group 49B.

*Sepals.*—Color: Green Group 138B, except when exposed to bright sunlight. Then it is Greyed-Purple Group 184C. Surface Texture: Covered in fine hairs. There are three lightly appendaged sepals. There are two unappendaged sepals with hairy edges.

*Receptacle.*—Color: Green Group 137C with, in bright direct sunlight, some areas of Greyed-Purple Group 184C. Shape: Funnel. Size: Medium (about ⅜ inch× 3⁄16 inch). Surface: Smooth.

*Peduncle.*—Length: Medium, about 3 to 3½ inches). Surface: Rough, prickly and glandular. Color: Greyed-Purple Group 183A. Strength: Stiff; erect.

Bloom:

*Size.*—Large. Average open size is 4½ inches.

*Borne.*—Singly.

*Stems.*—Strength: Strong. Average length is about 18–22 inches.

*Form.*—When first open, bloom is high centered. Permanence: Retains its form to the end; outer petals curl back.

*Petalage.*—Number of petals under normal conditions: 30–35.

*Color.*—The upper sides of the petals are Red Group 49D, except the lower ¼ of the petal, which is Yellow Group 11C with a dark yellow color spot. The reverse sides of the petals are Red Group 49C, except on the petal edge where there is a darker border of Red Group 49B. The base of each petal has on the upper surface a 3/16 inch×3/16 inch, Yellow Group 6C color spot. The lower surface has a 3/16 inch×3/16 inch, Yellow 6D color spot. The major color on the upper side is Red Group 49D.

*Variegations.*—On the guard petals are greenish streaks along the upper surface mid rib. On the lower surface, the greenish mid rib is also present as well as Red Group 53C sport and blotches.

*Discoloration.*—The general tonality at the end of the first day: No change. At the end of the third day: No change.

*Fragrance.*—Strong; sweet (cotton candy).

Petals:

*Texture.*—Thick.

*Shape.*—Round to deltoid.

*Form.*—Tips slightly recurved.

*Arrangement.*—Imbricated. There are no pealoids in the center.

*Persistence.*—Petals drop off cleanly before drying.

*Lastingness.*—On the plant: Long (about seven to eight days). As a cut flower: Long (about nine to ten days).

Reproductive parts:

*Anthers.*—Size: Medium. Quantity: Many. Color: Yellow-Orange Group 18B. Arrangement: Regular around styles.

*Filaments.*—Color: Yellow-Orange Group 14C.

*Pollen.*—Present.

*Styles.*—Color: Red Group 53B.

*Stigmas.*—Color: Orange-White Group 159C.

Plant

*Form.*—Bush.

*Growth.*—Very vigorous; upright; branching. At maturity, height is 6 feet, width is 4½ feet.

Foliage: Number of leaflets on normal mid-stem leaves: Five or seven.

*Size.*—Large (6 inches long×4 inches wide).

*Quantity.*—Abundant.

*Color.*—New foliage: Upper and lower surfaces: Greyed-Purple Group 183A. Old foliage: Upper surface: Green Group 139A. Lower surface: Green Group 139B.

Leaflets:

*Shape.*—Pointed oval.

*Textuure.*—Leathery; glossy.

*Edge.*—Serrated.

*Serration.*—Single; small.

*Petiole rachis.*—Color: Upper: Green Group 139A. Lower: Yellow-Green Group 147B.

*Petiole underside.*—Rough, with prickles and glands.

*Stipules.*—Medium (about ¾ inch); serrated; bearded.

*Disease resistance.*—Resistant to rust; susceptible to mildew and blackspot under normal growing conditions.

Wood:

*New wood.*—Color: Greyed-Purple Group 183A. Bark: Smooth.

*Old wood.*—Color: Green Group 137A. Bark: Smooth.

Prickles:

*Quantity.*—One main canes from base: Ordinary. On laterals from main canes: Ordinary.

*Form.*—Medium; hooked downward.

*Color when young.*—Greyed-Purple Group 183A.

*Color when mature.*—Greyed-Orange Group 165C.

Small prickles:

*Quantity.*—On main stalks: None. On laterals: None.

I claim:

1. A new and distinct variety of rose plant of the hybrid tea class, substantially as herein shown and described, characterized particularly by its free flowering of pinkish flowers having a high centered bud and open flower form on long stems; strong fragrance; and vigorous, upright, well-branched growth.

* * * * *

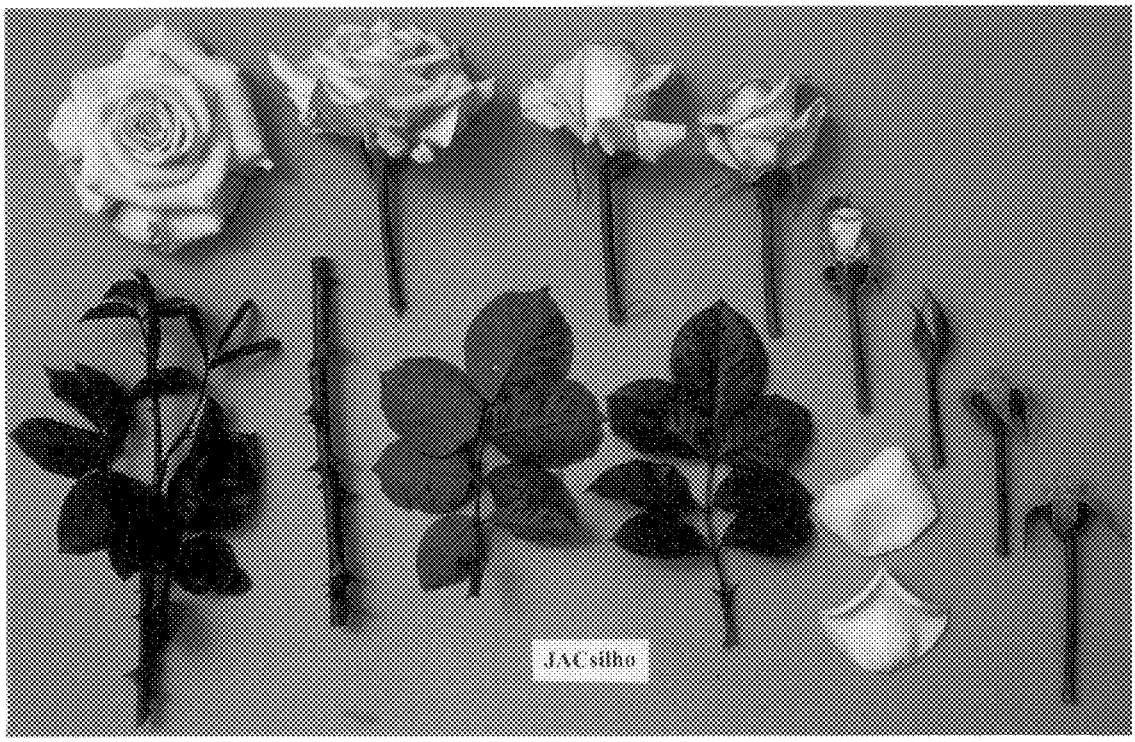
JAC silho

UNITED STATES PATENT AND TRADEMARK OFFICE

CERTIFICATE OF CORRECTION

PATENT NO. : PP 12,127 E
DATED : October 9, 2001
INVENTOR(S) : Keith W. Zary Ph.D.

It is certified that error appears in the above-identified patent and that said Letters Patent is hereby corrected as shown below:

Column 2,
Line 23, "borderof" should read -- border of --
Line 33 "inches)." should read -- inches. --

Column 3,
Line 20, "sport" should read -- spots --
Line 29, "pealoids" should read -- petaloids --

Column 4,
Line 11 "Textuure." should read -- Texture. --
Line 29, "One" should read -- On --

Signed and Sealed this

Nineteenth Day of March, 2002

*Attest:*

*Attesting Officer*

JAMES E. ROGAN
*Director of the United States Patent and Trademark Office*